US010443082B2

(12) United States Patent
Tong et al.

(10) Patent No.: US 10,443,082 B2
(45) Date of Patent: Oct. 15, 2019

(54) CONCENTRATION GRADIENT TEST REAGENT KIT AND TESTING METHOD FOR USE IN BACTERIAL/FUNGAL DRUG SUSCEPTIBILITY TESTING

(71) Applicant: XINTRUM PHARMACEUTICALS, LTD, Nanjing (CN)

(72) Inventors: Mingqing Tong, Nanjing (CN); Dong Jin, Nanjing (CN); Yi Zhang, Nanjing (CN)

(73) Assignee: XINTRUM PHARMACEUTICALS, LTD, Nanjing (CN)

( * ) Notice: Subject to any disclaimer, the term of this patent is extended or adjusted under 35 U.S.C. 154(b) by 360 days.

(21) Appl. No.: 15/118,958

(22) PCT Filed: Aug. 27, 2014

(86) PCT No.: PCT/CN2014/085310
§ 371 (c)(1),
(2) Date: Aug. 15, 2016

(87) PCT Pub. No.: WO2015/120712
PCT Pub. Date: Aug. 20, 2015

(65) Prior Publication Data

US 2017/0058312 A1 Mar. 2, 2017

(30) Foreign Application Priority Data

Feb. 15, 2014 (CN) .......................... 2014 1 0051738

(51) Int. Cl.
*C12Q 1/18* (2006.01)
*C12M 1/32* (2006.01)
*C12M 1/12* (2006.01)

(52) U.S. Cl.
CPC ............... *C12Q 1/18* (2013.01); *C12M 23/12* (2013.01); *C12M 25/14* (2013.01)

(58) Field of Classification Search
CPC .......... C12Q 1/18; C12M 23/12; C12M 25/14
See application file for complete search history.

(56) References Cited

FOREIGN PATENT DOCUMENTS

CN 202139239 * 8/2011 .............. C12M 1/34
CN 103421686 * 5/2012 .............. C12M 1/34

* cited by examiner

*Primary Examiner* — Jana A Hines
(74) *Attorney, Agent, or Firm* — Yong Chen; Lin Sun-Hoffman; Liu Chen & Hoffman LLP

(57) ABSTRACT

The present invention discloses a concentration gradient test reagent kit and a testing method for use in bacterial/fungal drug susceptibility testing. The reagent kit includes a test strip unit. The test strip unit includes a strip-shaped culture medium container and a drug container. The culture medium container and the drug container comprise axially-arranged culture medium cells and drug cells, respectively. The culture medium cells can be inserted into corresponding drug cells. The drug container and the culture medium container are stable, easy to preserve and transport, and can be included into a reagent kit for long-term storage. The kit allows for easy and convenient testing operations. Testing results are easy to observe and interpret. The kit can be used in drug susceptibility testing on slow-growing fungi and anaerobic bacteria. Testing procedures and waste processing is biologically very safe.

12 Claims, 3 Drawing Sheets

1
2
3
4
5
8
7
6
9

CONCENTRATION GRADIENT TEST REAGENT KIT AND TESTING METHOD FOR USE IN BACTERIAL/FUNGAL DRUG SUSCEPTIBILITY TESTING

CROSS REFERENCES TO RELATED APPLICATIONS

This application is a national stage application under 35 U.S.C. 371 based on and claiming the benefit of International Application PCT/CN2014/085310, filed on Aug. 27, 2014, which claims the benefit of priority from Chinese Application No. 201410051738.0, filed Feb. 15, 2014, the entire disclosure of each of which is incorporated herein by reference.

BACKGROUND OF THE INVENTION

1. Technical Field

The present invention relates to a concentration gradient test reagent kit and a testing method for use in bacterial/fungal drug susceptibility testing and falls within the technical field of drug assay apparatuses and assay methods.

2. Description of Related Art

Common methods for use in performing susceptibility testing on antimicrobial drugs include a paper method, a dilution method, and an E-test method. The paper method for performing drug susceptibility testing is a qualitative testing method which is convenient but provides little information to compare and choose between susceptible drugs. The dilution method includes broth dilution method and agar dilution method. The broth method includes the tube dilution method and the microdilution method. The tube dilution method often requires intricate operations and thus not suitable in voluminous or batch tests. Although the microdilution method requires smaller amounts of reagents and specimens than the tube dilution method, the microdilution method is not only more complicated but also less clear in result reading than the tube dilution method. The agar dilution method is more suitable for tests involve large amounts of specimen, but is not suitable for occasional tests of sporadic clinical specimen, requires the preparation of a drug-containing culture plate and at the time of testing, and quite cumbersome. Although the E-test method has certain advantages of both the paper method and the dilution method, e.g., the convenience of the paper method, and the ability to determine MIC of the dilution method, it is expensive and not as accurate in terms of MIC results. Thus, common methods for performing antimicrobial drug susceptibility testing according to the prior art no longer meet people's needs.

SUMMARY OF THE INVENTION

The objective of the present invention is to provide a concentration gradient test reagent kit and a testing method for use in bacterial/fungal drug susceptibility testing that meet current clinical needs, is applicable to both single specimen tests as well as batch specimen operations, is accurate and convenient, and allows different antibiotics and agar to be premade and freely combined as needed, and enables qualitative and quantitative determination of MIC, thereby addressing an otherwise unattended issue in this technical field, meeting the market's urgent needs, and overcoming the drawbacks of the prior art.

The present invention is implemented by a technical solution described below.

A concentration gradient test reagent kit for use in bacterial/fungal drug susceptibility testing is provided. The reagent kit comprises a test strip unit(s). A test strip unit comprises a strip-shaped culture medium container and a strip-shaped drug container. The culture medium container and the drug container comprise axially-arranged culture medium cells and drug cells, respectively. The culture medium cells are insertable into the corresponding drug cells. The culture medium cells each have therein a prefabricated solid culture medium. The inner wall of the bottom of each drug cell has a convex surface, on which an antimicrobial drug is disposed.

In certain specific embodiments, a mid-section of the inner wall of each culture medium cell is defined with a waist line which is a protrusion projecting in the direction of a central axis.

In certain specific embodiments, the concentration gradient test reagent kit further comprises a box-shaped culture holder which has a hollowed-out channel(s) with which the test strip unit(s) can be engaged and fitted.

In certain specific embodiments, sheet-shaped, separable plastic films are disposed on the top and bottom of the culture medium container, respectively.

In certain specific embodiments, a control mark panel is disposed on one side of the box-shaped culture holder.

In certain specific embodiments, the control mark panel comprises a positive control mark, a negative control mark, and numeric graduation marks.

The present invention further provides a method of manufacturing a concentration gradient test reagent kit for use in bacterial/fungal drug susceptibility testing, characterized in that the method comprises the steps of:

(1) manufacturing a drug container, a drug container lid, a body of a culture medium container, a bottom of a culture medium container, a box-shaped culture holder, and a culture medium package case by compression molding;

(2) sterilizing the drug container, the drug container lid, the body of the culture medium container, and the bottom of the culture medium container;

(3) in a relatively sterile environment, introducing an amount of an antimicrobial drug solution into cells of the drug container, and vacuum drying the drug container cells;

(4) adhering a plastic film to the bottom of the culture medium container;

(5) using a liquid culture medium as a solute to prepare a sol of a predetermined concentration in a sterile condition, and introducing the sol into cells of the culture medium container, solidifying the sol so as to form a solid culture medium, and sealing a plastic film on the upper surface of the culture medium container;

(6) in a sterile environment, packaging the drug container and the drug container lid in a plastic bag or plastic box;

(7) placing a plurality of the culture medium containers in a culture medium package case; and (8) sterilizing the plastic box containing the drug container and drug container lid, and the packaged case containing culture medium containers with cobalt-60 irradiation.

The beneficial technical effects of the present invention are as follows: the drug container and the culture medium container are stable, easy to preserve and transport, and can be included into a reagent kit for long-term storage; the kit allows for easy and convenient testing operations; testing results are easy to observe and interpret; the kit can be used in drug susceptibility testing on slow-growing fungi and anaerobic bacteria; testing procedures and waste processing is biologically very safe.

DETAILED DESCRIPTION OF EMBODIMENTS

Figure 1:
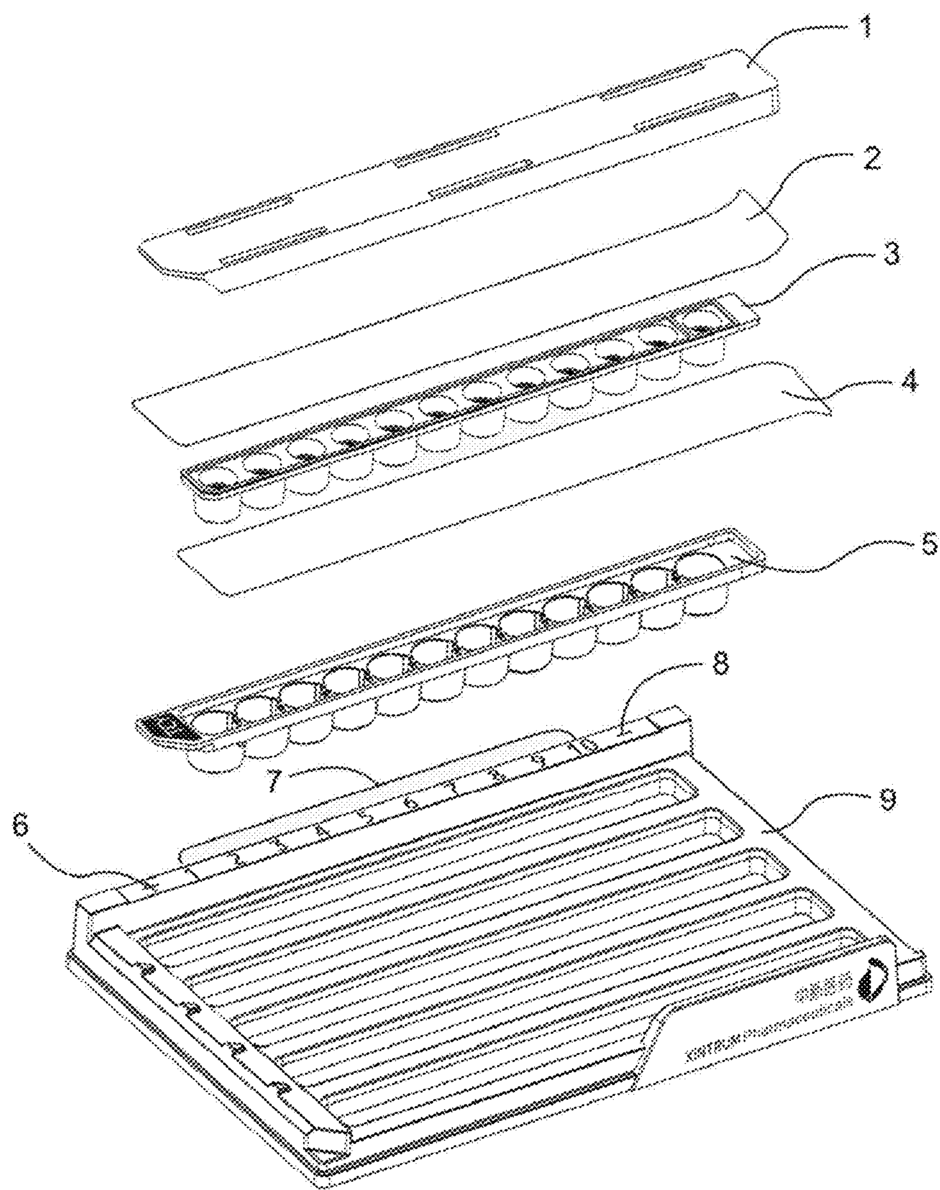
FIG. 1 is an exploded view of a test reagent kit of the present invention.
Figure 2:
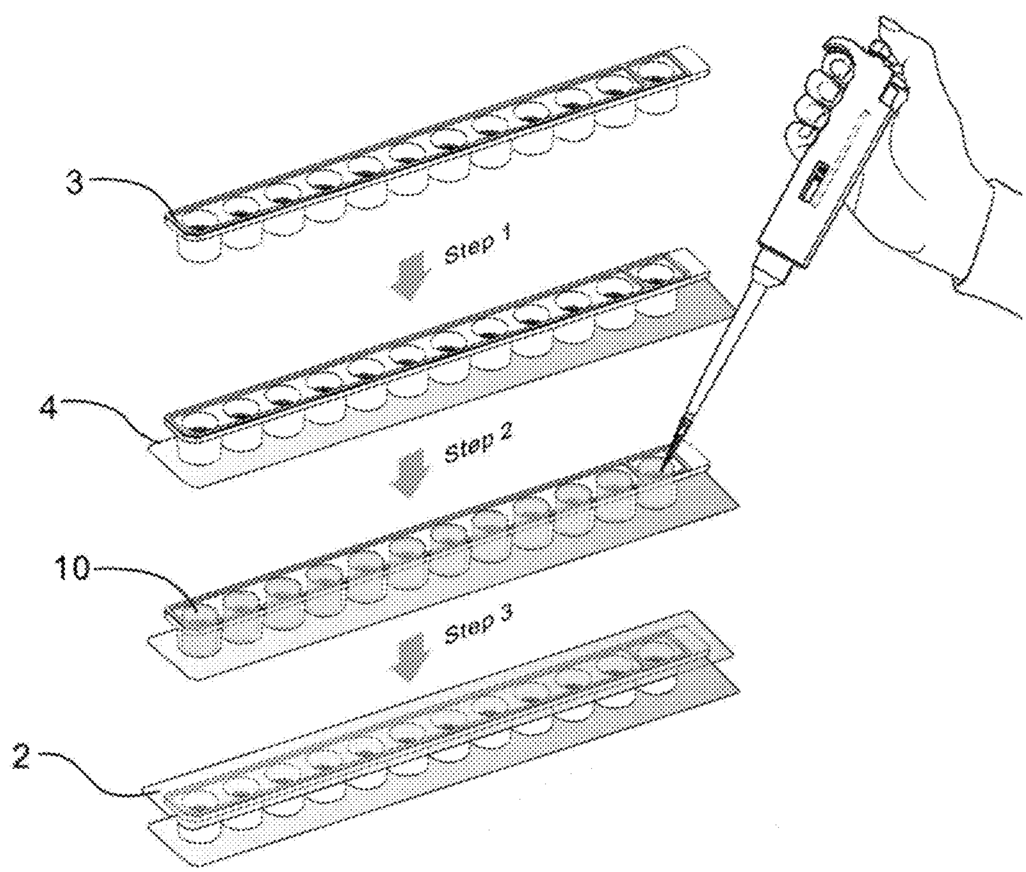
FIG. 2 is a schematic view of the operation steps for a culture medium container and plastic films.
Figure 3:
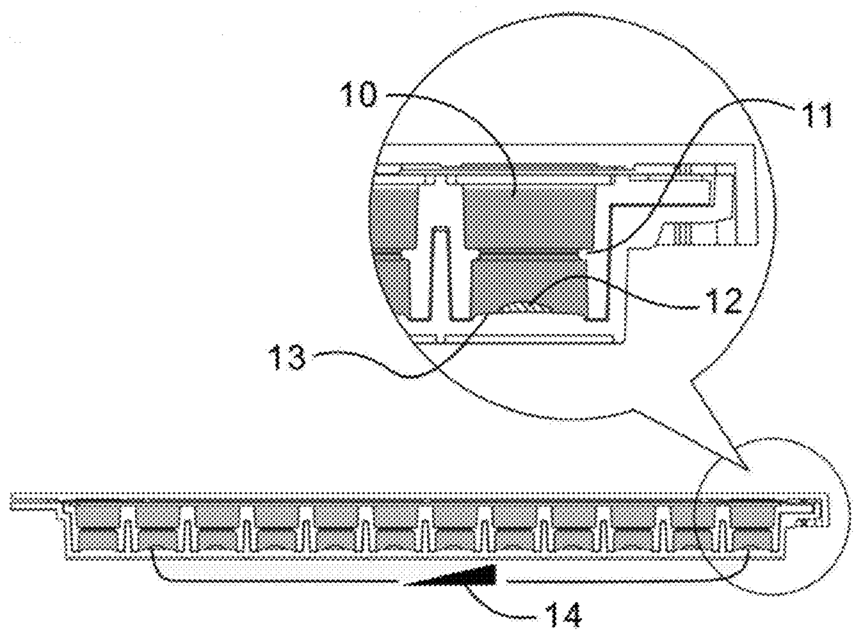
FIG. 3 is a partial enlarged view of cells after the culture medium container has been inserted into a drug container (i.e., after a test strip unit has been assembled)
Figure 4:
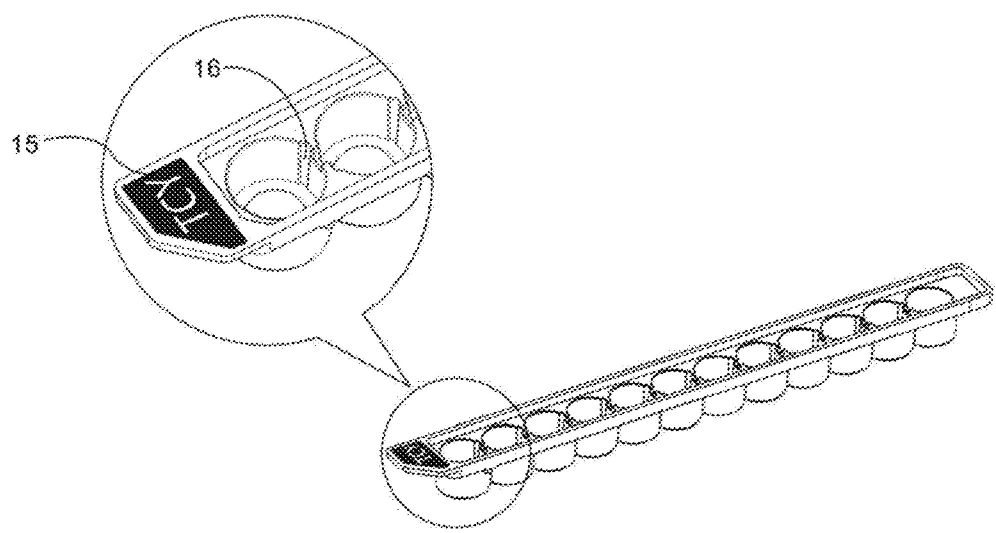
FIG. 4 is a partial enlarged view of the drug container.

Embodiments of the present invention are described below to help the general public understand the present invention, but the specific embodiments described herein by the applicant cannot and should not be regarded as limitations on the technical solution of the present invention, as any changes made to the definitions of technical features or components of the present invention and/or any alterations made to the overall structure that are merely formal but non-substantive should be deemed to be within the scope of protection defined by the technical solution of the present invention.

References in the drawings include: drug container lid 1, top plastic film 2, culture medium container 3, bottom plastic film 4, drug container 5, positive control mark 6, numeric graduation marks 7, negative control mark 8, box-shaped culture holder 9, culture medium 10, waist line 11, antimicrobial drug 12, convex surface 13, drug concentration gradient 14, drug name mark 15, venting groove 16.

A concentration gradient test reagent kit for use in bacterial/fungal drug susceptibility testing is provided. The test reagent kit comprises a test strip unit. The test strip unit comprises a strip-shaped culture medium container 3 and a drug container 5. The culture medium container 3 and the drug container 5 comprise axially-arranged culture medium cells and drug cells, respectively. The culture medium cells are insertable into the corresponding drug cells. The test reagent kit further comprises a box-shaped culture holder 9. The box-shaped culture holder 9 has a hollowed-out channels with which the test strip units can be engaged and fitted. The test reagent kit has thereon a drug container lid 1. A control mark panel is disposed on one side of the box-shaped culture holder 9. The control mark panel comprises a positive control mark 6, a negative control mark 8, and numeric graduation marks 7. Each test strip unit measures an MIC of a drug. The test strip units can be grouped as needed and disposed in the box-shaped culture holder 9, and placed in a certain culture environment, where the MIC of a test strain can be measured with respect to a multitude of drugs. The box-shaped culture holder 9 is a box-shaped object with a rectangular profile. The test strip units, each of which comprises a drug container 5 and a culture medium container 3, can be transversely placed on the culture holder 9. Each box-shaped culture holder 9 can accommodate 5 test strips. A lateral periphery of the upper surface of the culture holder 9 is marked with signs "+", "−" and numerals. A foolproof design is included at longitudinal ends of the upper surface of the box-shaped culture holder 9, such that the test strip units can be inserted into the box-shaped culture holder 9 only in a specific direction. The box-shaped culture holder 9 may be reusable.

In this embodiment, the cells of culture medium container 3 and drug container 5 are arranged in a row and form cell groups, where neighboring cells are closely juxtaposed. Certainly, in other embodiments, the number and configuration of the cells may be varied as needed to meet the needs in different situations. Therefore, this embodiment is not restrictive of the present invention. Sheet-shaped, separable plastic films are disposed on the top and bottom of the culture medium container 3, respectively. The plastic films include a top plastic film 2 and a bottom plastic film 4. The top and bottom plastic films 2, 4 are fixed to the upper and lower surfaces of the culture medium container 3 by adhesion, respectively. The culture medium cells each have therein a pre-fabricated solid culture medium. The inner wall of the bottom of each drug cell includes a convex surface. An antimicrobial drug is disposed on the convex surface. A mid-section of the inner wall of each culture medium cell is defined with a waist line 11 which is a protrusion projecting in the direction of a central axis.

In this embodiment, the drug container 5 is technically characterized in that the drug container cells each hold a drug with different concentrations which have been pre-calculated and prepared in advance, and that the drug of different concentrations is physically separated. The bottom of each drug container cell has a convex surface and holds a dry antimicrobial drug. The amounts of the antimicrobial drug in the consecutively-arranged drug container cells are arranged in an ascending (or descending) order. The inner wall of each cell includes a plurality of venting grooves 16 such that, upon insertion of the culture medium container 3, air can be pushed out through the venting grooves 16. A drug name mark 15 is included at one end of the drug container 5. The drug name mark 15 bears colors and alphabets which not only indicate the name of the drug contained in the drug container 5 but also ensure that a user can correctly discern the direction of the drug concentration gradient. Antibiotics of different types are denoted by different chromatic system signs, respectively. Different antibiotics of the same type are denoted by different color signs of the same chromatic system, respectively.

In this embodiment, the culture medium container 3 is technically characterized in that: the culture medium container 3 comprises independent culture medium cells; the culture medium cells each have therein a pre-fabricated solid culture medium (which mainly comprises agar); the bottom of each culture medium cell can be removed; the inner wall of each culture medium cell is configured with waist line 11 which prevents the agar from coming off when the bottom is removed; after the bottom has been removed, the cells of the culture medium container can be inserted into the cells of the drug container, respectively; and, due to the design of the culture medium container, the pressure generated by the inward sliding of the drug container lid 1 causes the agar culture medium to come into contact with the antimicrobial drug disposed at the bottom of the drug container cells while maintaining the breathability of the culture medium. The culture medium container 3 is preloaded with a culture medium. The volume of the culture medium container 3 is designed to allow the antibiotic disposed in the drug cell to attain a predetermined concentration when dissolved. The composition of the culture medium can be selected to be suitable for different bacteria and/or fungus having varying requirements for growth, and can be stored for a long period of time. One culture medium container 3 and one drug container 5 together can form a drug susceptibility test strip unit, and each test strip unit can be used to determine a drug's MIC. Multiple test strip units may be grouped as needed.

Pre-fabrication of an antimicrobial concentration gradient: a strip-shaped plastic drug container has a series of divisions (drug container cells), and ascending (or descending) amounts of an antimicrobial drug solution are added to the bottoms of the divisions (drug container cells). The antimicrobial drug solution is dried under a negative pressure and then covered with a lid so as to be preserved at 4° C. for later use.

Pre-fabrication of a culture medium based in agar (or another gel): a sol solution is prepared from a broth culture medium for culturing bacteria, and then the sol solution is added to the series of cells of a strip-shaped culture medium container. The sol is then solidified physically (such as by lowering the temperature) or chemically, and the solid gel is packaged and sealed, and preserved at 4° C. for later use.

Combination of the pre-fabricated antimicrobial drug and pre-fabricated culture medium to form a test strip unit: the films are removed from the bottom and top of the culture medium container, and the cells of the culture medium container can be inserted into the corresponding cells of the drug container. Then, the drug container is covered with a lid, and the pressure created in the process causes the antimicrobial drug at the bottoms of the cells to come into contact with the solid culture medium, and therefore dissolved in the agar culture medium to reach a specific concentration. To use the solid culture medium, a bacterial culture solution can be applied on the upper surface of the solid culture medium in each cell of the culture medium container. Then the culture medium container is covered with a lid, and then kept at 35° C. for 16-20 hours before the culture result is visually checked. When the drug concentration is higher than the MIC for the bacteria, no bacteria is observed on the surface of the gel. When the drug concentration is lower than the MIC, the bacteria grows on the surface of the culture medium and eventually develops a bacterial colony thereon. The lowest drug concentration at which no bacteria is observed on the gel surface is considered as the MIC of the antimicrobial drug for the strain under test.

A method of manufacturing a test strip unit includes the following steps:

1) manufacturing a drug container 5, a drug container lid 1, the body of a culture medium container 3, the bottom of a culture medium container 3, a box-shaped culture holder 9, and a culture medium package case by compression molding;
2) sterilizing the drug container 5, the drug container lid 1, the body of the culture medium container 3, and the bottom of the culture medium container 3;
3) in a relatively sterile environment, introducing an amount of an antimicrobial drug solution into cells of the drug container, and vacuum drying the drug container cells;
4) adhering a plastic film to the bottom of the culture medium container 3;
5) using a liquid culture medium as a solute to prepare a sol of a predetermined concentration in a sterile condition, and introducing the sol into cells of the culture medium container 3, solidifying the sol so as to form a solid culture medium, and sealing a plastic film on the upper surface of the culture medium container 3;
6) in a sterile environment, packaging the drug container 5 and the drug container lid 1 in a plastic bag or plastic box;
7) placing a plurality of the culture medium containers 3 in a culture medium package case; and
8) irradiating the large-packaged drug container 5 and culture medium container with cobalt-60 to sterilize them and then storing them at a room temperature or 4° C.

Embodiments of a method of performing concentration gradient measurement for use in bacterial/fungal drug susceptibility testing are described below.

Embodiment 1

A concentration gradient measurement method for use in bacterial/fungal drug susceptibility testing is provided. The method comprises the steps of:

1) irradiating drug container and culture medium container manufactured by compression molding to sterilize them;
2) adding Cefotaxime with concentrations of 3.75, 7.5, 15.0, 30.0, 60.0, 120.0, 240.0, 480.0, 960.0, 1920.0 μg/ml into the second to eleventh cells (and not the first and twelfth cells) of the drug container, 13 μl of Cefotaxime each, and drying the drug container under a negative pressure for later use;
3) adding 1.2% agar to MH broth, dissolving the agar by boiling water insulated from the agar, sterilizing the agar under high pressure at 121° C. for 15 minutes;
4) pipetting a 1.2% hot agar solution to a culture medium container under a sterile condition, the culture medium container having round cells each with internal dimensions of a bottom's radius of 3.25 mm and a height of 6 mm, with gel strips each being of a thickness of about 6 mm, wherein, after the agar solution has cooled and solidified, the solid agar is packaged in a culture medium package case for later use;
5) inoculating a nutrient agar plate with various test strains (see Table 1), cultivating the test strains at 35° C. overnight, taking 4 or 5 colonies having the same pattern from the pure culture plate in the following day, making a uniform bacterial suspension from the colonies with normal saline and adjusting its turbidity to 0.5 McFarland standard;
6) removing the film from the bottom of the agar culture medium container, inserting the agar culture medium container into the drug container so that the antibiotic in the drug container disperses into the agar, thereby allowing the drugs in the drug-containing cells to reach final concentrations of 0.25, 0.5, 1.0, 2.0, 4.0, 8.0, 16.0, 32.0, 64.0 and 128.0 μg/ml, respectively;
7) dipping a swab in a bacterial solution of 0.5 McFarland standard to apply the bacterial solution to the surface of the agar block in each cell in a direction from the left to the right, with increasing concentrations of the bacterial solution; sliding close the drug container lid in a direction from the right to the left, and then placing the test strip unit into a moist box to incubate at 37° C. for 16-20 hours before visually observing the result, wherein the lowest drug concentration in a cell where there is no bacterial growth is considered the MIC value of the drug. The bacterial lawn on the drug-free control agar blocks is expected to grow well; and
8) in the meantime, performing an MIC assay on the test strains with tube broth dilution method.

Embodiment 2

This embodiment still uses a drug container with 12 round cells, and each round cell has internal dimensions of 4 mm×6 mm (bottom's radius×height). However, the experimental strains in use are *Streptococcus pneumoniae*. The related manufacturing and testing processes are as follows:

1) irradiating drug container and culture medium container, which are manufactured by compression molding, to sterilize them;
2) putting Amoxicillin with concentrations of 0.9, 1.8, 3.75, 7.5, 15, 30, 60, 120, 240, 480 μg/ml in the second to eleventh cells, rather than the first and twelfth cells, of the drug container, 13 μl of Amoxicillin each, drying the drug container under a negative pressure for later use;
3) adding 1.2% agar to CAMHB broth, dissolving the agar by boiling the broth while being insulated from water, sterilizing the agar under a high pressure at 121° C. for 15 minutes, sterilizing the agar as soon as its temperature drops to 50° C., mixing the sterilized agar with 2.5% LHB, wherein the CAMHB broth is a regulated cation concentration MH broth;
4) pipetting a hot agar solution to a culture medium container in a sterile condition, wherein each round cell of the culture medium container has internal dimensions of a bottom's radius 3.25 mm×a height of 6 mm, and each gel strip is 6 mm thick approximately, wherein, after the agar solution has cooled and solidified, the solid agar is packaged in a culture medium package case for later use;
5) inoculating a sheep blood agar plate with various test strains (see Table 2), cultivating the test strains at 35° C. with 5% $CO_2$ overnight, taking 4 or 5 colonies having a same pattern from the pure culture plate the following day, making a uniform bacterial suspension from the colonies with normal saline, and adjusting its turbidity to 0.5 McFarland standard;
6) removing the film from the bottom of the agar culture medium container, inserting the agar culture medium container into the drug container so that the antibiotic in the drug container disperses into the agar, thereby allowing the drugs in the drug-containing cells to reach final concentrations of 0.06, 0.12, 0.25, 0.5, 1.0, 2.0, 4.0, 8.0, 16 and 32 μg/ml, respectively;
7) dipping a swab in a bacterial solution of 0.5 McFarland standard to apply the bacterial solution to the surface of the agar block in each cell in a direction from the left to the right, with increasing concentrations of the bacterial solution, sliding close the drug container lid in a direction from the right to the left; and then placing the test strip unit into a moist box to incubate at 37° C. for 16-20 hours before visually observing the result; wherein the lowest drug concentration in a cell where there is no bacterial growth is considered the MIC value of the drug. The bacterial lawn on the drug-free control agar blocks is expected to grow well; and
8) performing an MIC assay on the test strains with the tube broth dilution method.

The measurement results of the two methods are shown in Table 2.

TABLE 1

Comparison of the results (mg/L) of MIC assays performed on 30 pathogens by this method and tube broth dilution method with Cefotaxime

| Strain No. | Strain Name | Concentration (gradient agar strip method) | Concentration (tube broth dilution method) |
|---|---|---|---|
| 1 | *Klebsiella pneumoniae* | 4.0 | 4.0 |
| 2 | *Klebsiella pneumoniae* | 4.0 | 4.0 |
| 3 | *Klebsiella pneumoniae* | 4.0 | 2.0 |
| 4 | *Klebsiella pneumoniae* | 2.0 | 2.0 |
| 5 | *Klebsiella pneumoniae* | 2.0 | 2.0 |
| 6 | *Klebsiella pneumoniae* | 4.0 | 4.0 |
| 7 | *Klebsiella pneumoniae* | 8.0 | 8.0 |
| 8 | *Klebsiella pneumoniae* | 4.0 | 4.0 |
| 9 | *Escherichia coli* | 8.0 | 8.0 |
| 10 | *Escherichia coli* | 1.0 | 1.0 |
| 11 | *Escherichia coli* | 2.0 | 4.0 |
| 12 | *Escherichia coli* | 4.0 | 4.0 |
| 13 | *Escherichia coli* | 4.0 | 4.0 |
| 14 | *Escherichia coli* | 8.0 | 8.0 |
| 15 | *Escherichia coli* | 2.0 | 4.0 |
| 16 | *Escherichia coli* | 4.0 | 4.0 |
| 17 | *Escherichia coli* | 4.0 | 4.0 |
| 18 | *Klebsiella pneumoniae* | 16.0 | 16.0 |
| 19 | *Escherichia coli* | 16.0 | 16.0 |
| 20 | *Escherichia coli* | 4.0 | 4.0 |
| 21 | *Klebsiella pneumoniae* | 8.0 | 8.0 |
| 22 | *Klebsiella oxytoca* | 8.0 | 8.0 |
| 23 | *Escherichia coli* | 8.0 | 8.0 |
| 24 | *Klebsiella pneumoniae* | 4.0 | 4.0 |
| 25 | *Klebsiella oxytoca* | 8.0 | 8.0 |
| 26 | *Escherichia coli* | 4.0 | 4.0 |
| 27 | *Proteus mirabilis* | 8.0 | 4.0 |
| 28 | *Enterobacter cloacae* | 16.0 | 16.0 |
| 29 | *Enterobacter cloacae* | 16.0 | 16.0 |
| 30 | *Escherichia coli* | 8.0 | 8.0 |

TABLE 2

Comparison of the results (μg/ml) of MIC assays performed on 20 strains of *Streptococcus pneumoniae* by this method and tube broth dilution method with Amoxicillin

| Strain No. | Strain Name | Concentration (gradient agar strip method) | Concentration (tube broth dilution method) |
|---|---|---|---|
| 1 | *Streptococcus pneumoniae* | 0.12 | 0.12 |
| 2 | *Streptococcus pneumoniae* | 0.12 | 0.12 |
| 3 | *Streptococcus pneumoniae* | 0.25 | 0.12 |
| 4 | *Streptococcus pneumoniae* | 0.25 | 0.25 |
| 5 | *Streptococcus pneumoniae* | 0.5 | 0.5 |
| 6 | *Streptococcus pneumoniae* | 0.12 | 0.12 |
| 7 | *Streptococcus pneumoniae* | 0.25 | 0.25 |
| 8 | *Streptococcus pneumoniae* | 1.0 | 0.5 |
| 9 | *Streptococcus pneumoniae* | 0.25 | 0.25 |
| 10 | *Streptococcus pneumoniae* | 2.0 | 2.0 |
| 11 | *Streptococcus pneumoniae* | 0.12 | 0.12 |
| 12 | *Streptococcus pneumoniae* | 0.06 | 0.06 |
| 13 | *Streptococcus pneumoniae* | 0.06 | 0.12 |
| 14 | *Streptococcus pneumoniae* | 2.0 | 2.0 |
| 15 | *Streptococcus pneumoniae* | 0.12 | 0.12 |
| 16 | *Streptococcus pneumoniae* | 0.12 | 0.12 |
| 17 | *Streptococcus pneumoniae* | 1.0 | 1.0 |
| 18 | *Streptococcus pneumoniae* | 0.5 | 1.0 |
| 19 | *Streptococcus pneumoniae* | 0.25 | 0.12 |
| 20 | *Streptococcus pneumoniae* | 0.12 | 0.12 |

Explanation of the results: as shown in Table 1 and Table 2, this method (concentration gradient agar strip method) yields mostly the same result as the tube broth dilution method, except for an occasional difference of a titer of 1:2. However, since the methodological permissible errors for the broth dilution method fall within the range of a titer of 1:2 lower to a titer of 1:2 higher, the results of the concentration gradient agar strip method are consistent with the results of the dilution method.

Embodiment 3 a drug container which has 12 round cells each with internal dimensions of 4 mm×6 mm (bottom's radius×height), and a culture medium container which has 12 round cells each with internal dimensions of 3.25 mm×6 mm (bottom's radius×height). The gel strips are made of agar gel.

Embodiment 4 a drug container which has 12 round cells each with internal dimensions of 4 mm×6 mm (bottom's radius×height), and a culture medium container which has 12 round cells each with internal dimensions of 3.25 mm×6 mm (bottom's radius×height). The gel strips are made of polyacrylamide gel.

Embodiment 5 a drug container which has 12 round cells each with internal dimensions of 4 mm×6 mm (bottom's radius×height), and a culture medium container which has 12 round cells each with internal dimensions of 3.25 mm×6 mm (bottom's radius×height). The gel strips are made of plant protein adhesive.

Embodiment 6 a drug container which has 12 round cells each with internal dimensions of 4 mm×6 mm (bottom's radius×height), and a culture medium container which has 12 round cells each with internal dimensions of 3.25 mm×6 mm (bottom's radius×height). The gel strips are made of gelatin gel.

The present invention also has some other embodiments. Persons skilled in the art can make various changes and modifications to the present invention without departing from the spirit and essential features of the present invention. However, the changes and modifications are deemed covered by the appended claims of the present invention.

What is claimed is:

1. A concentration gradient test reagent kit for use in bacterial/fungal drug susceptibility testing, comprising:

a test strip unit, the test strip unit comprising a strip-shaped culture medium container and a drug container, wherein the culture medium container and the drug container comprise axially-arranged culture medium cells and drug cells, respectively, wherein the culture medium cells can be inserted into the corresponding drug cells, with each said culture medium cell having therein a pre-fabricated solid culture medium, each said culture medium cell having a bottom removable before the cell inserted into a corresponding one of the drug cells, wherein an inner wall of a bottom of each said drug cell has a convex surface, and an antimicrobial drug of different concentrations are disposed on the convex surface and include a positive control and negative control, and wherein the inner side of a side wall of each said drug cell includes a venting groove.

2. The concentration gradient test reagent kit for use in bacterial/fungal drug susceptibility testing according to claim 1, wherein a mid-section of the inner wall of each culture medium cell is defined with a waist line which is a protrusion projecting in the direction of a central axis.

3. The concentration gradient test reagent kit for use in bacterial/fungal drug susceptibility testing according to claim 1, wherein the concentration gradient test reagent kit further comprises a box-shaped culture holder which includes a hollowed-out channel with which the test strip unit can be engaged and fitted.

4. The concentration gradient test reagent kit for use in bacterial/fungal drug susceptibility testing according to claim 1, wherein that sheet-shaped, separable plastic films are disposed on a top and bottom of the culture medium container, respectively.

5. The concentration gradient test reagent kit for use in bacterial/fungal drug susceptibility testing according to claim 1, wherein each drug cell includes a venting groove, and the venting groove is vertically disposed on the inner wall of the drug cell.

6. The concentration gradient test reagent kit for use in bacterial/fungal drug susceptibility testing according to claim 3, wherein a control mark panel is disposed on one side of the box-shaped culture holder.

7. The concentration gradient test reagent kit for use in bacterial/fungal drug susceptibility testing according to claim 6, wherein the control mark panel comprises a positive control mark, a negative control mark, and numeric graduation marks.

8. The concentration gradient test reagent kit for use in bacterial/fungal drug susceptibility testing according to claim 2, wherein the concentration gradient test reagent kit further comprises a box-shaped culture holder which includes a hollowed-out channel with which the test strip unit can be engaged and fitted.

9. The concentration gradient test reagent kit for use in bacterial/fungal drug susceptibility testing according to claim 2, wherein that sheet-shaped, separable plastic films are disposed on a top and bottom of the culture medium container, respectively.

10. The concentration gradient test reagent kit for use in bacterial/fungal drug susceptibility testing according to claim 2, wherein each drug cell includes a venting groove, and the venting groove is vertically disposed on the inner wall of the drug cell.

11. The concentration gradient test reagent kit for use in bacterial/fungal drug susceptibility testing according to claim 8, wherein a control mark panel is disposed on one side of the box-shaped culture holder.

12. The concentration gradient test reagent kit for use in bacterial/fungal drug susceptibility testing according to claim 11, wherein the control mark panel comprises a positive control mark, a negative control mark, and numeric graduation marks.

* * * * *